(12) United States Patent
Trotta (10) Patent No.: US 6,325,790 B1
(45) Date of Patent: Dec. 4, 2001

(54) SOFT TIP CATHETER

(75) Inventor: Thomas N. Trotta, Miami Beach, FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/072,038

(22) Filed: May 4, 1998

Related U.S. Application Data (63) Continuation-in-part of application No. 08/420,290, filed on Apr. 11, 1995, now abandoned.

(51) Int. Cl.⁷ .................................................. A61M 25/00
(52) U.S. Cl. ......................... 604/523; 604/532; 604/264; 600/433
(58) Field of Search .................................. 604/523–528, 604/530–534, 264; 600/433–435

(56) References Cited

U.S. PATENT DOCUMENTS

| | | | |
|---|---|---|---|
| 4,034,015 | * 7/1977 | Hendrick et al. | 528/325 |
| 4,145,335 | * 3/1979 | Buxbaum et al. | 528/302 |
| 4,195,637 | 4/1980 | Gruntzig et al. . | |
| 4,368,090 | * 1/1983 | Mumcu et al. | 156/331.8 |
| 4,482,587 | * 11/1984 | Fagerburg et al. | 428/35 |
| 4,563,181 | * 1/1986 | Wijayarathna et al. | 604/523 |
| 5,045,072 | 9/1991 | Castillo et al. . | |
| 5,163,431 | * 11/1992 | Griep | 128/658 |
| 5,171,232 | 12/1992 | Castillo et al. . | |
| 5,300,048 | * 4/1994 | Drewes, Jr. et al. | 604/280 |
| 5,538,510 | 7/1996 | Fontirroche et al. . | |
| 5,545,708 | * 8/1996 | Onwunaka et al. | 528/76 |
| 5,658,263 | 8/1997 | Dang et al. . | |
| 5,769,830 | * 6/1998 | Parker | 604/523 |
| 5,820,594 | * 10/1998 | Fontirroche et al. | 604/96 |
| 5,827,242 | * 10/1998 | Follmer et al. | 604/523 |
| 5,849,846 | * 12/1998 | Chen et al. | 525/166 |
| 5,907,017 | * 5/1999 | Ober et al. | 525/332.3 |
| 5,951,941 | * 9/1999 | Wang et al. | 264/523 |
| 5,993,415 | * 11/1999 | O'Neil et al. | 604/96 |
| 6,177,523 | * 1/2001 | Reich et al. . | |

OTHER PUBLICATIONS

Rilsan, Transparent Copolymers, Rilsan 80.20–Rilsan 67.33, by Elf Atochem, Dec. 1991.*

General Chemistry, Principles and Modern Application, Ralph H. Petrucci and William S. Hardwood, Prentice Hall Copyright 1997, pp. 932–935 and 950–951.*

Engineered Materials Handbook, vol. 2, Engineering Plastics, Melvin I Kohan, ASM International Copyright 1988, pp. 124–127.*

* cited by examiner

*Primary Examiner*—Angela D. Sykes
*Assistant Examiner*—Patricia Bianco
(74) *Attorney, Agent, or Firm*—Watts Hoffman; Hoffman & Heinke

(57) ABSTRACT

In a torsion control catheter including a tubular body and a flexible tip connected to the tubular body, the improvement comprising a copolymer catheter tip composition comprising a first monomer of polyamide and a second monomer of polyamide having a lower alkyl side chain group attached to a polyamide backbone. The flexible catheter tip may include one or more tip members, at least one of which may be formed of the copolymer composition.

82 Claims, 2 Drawing Sheets

SOFT TIP CATHETER

This is a Continuation-in-Part application of application Ser. No. 08/420,290, filed on Apr. 11, 1995, now abandoned.

BACKGROUND OF THE INVENTION

This invention relates to a catheter, and in particular to a composition used in a torsion control catheter.

Torsion control catheters, such as angiographic or guiding catheters, are designed for intravascular use in the treatment of disease and typically have a soft, flexible tip member connected to a tubular body. The body is formed of a relatively stiff material such as a nylon or a stiff polyurethane to provide torqueability, burst pressure strength and longitudinal rigidity sufficient to advance the catheter in arteries and other tortious pathways in the body.

Torsion control catheters must be able to transmit a twisting or torsional force along their length to permit twisting forces applied at a proximal end portion of the body to be transmitted along the longitudinal axis of the catheter to the distal end portion of the body at which the tip is disposed. In this way, the catheter can be guided through arteries and the like. However, in doing so, the twisting and forward movement of the catheter poses a risk of injury or trauma to the surrounding tissue. Accordingly, it is generally desirable for such catheters to have a soft tip on one end of the body which is more flexible than the body. The soft tip prevents injury to the vessels and arteries as the catheter is advanced in the body and facilitates the guidability of the catheter.

Various polymer compositions for catheter bodies and for catheter soft tips have been proposed. Many of the catheter soft tips formed from these compositions suffer from limitations inherent in the thermal and/or physical properties of the tip materials. For example, some materials, such as polyamide block copolymers, exhibit too much memory. As a result, tips made from these materials tend to want to retain their shape, and may cause trauma to vessels when advanced in the body and may hinder guidability. Other materials do not bond well to commonly preferred body materials, or may become too soft at body temperature.

The present invention is directed to a catheter employing a soft tip having advantageous thermal and physical properties that overcome the problems associated with prior art catheters.

DESCRIPTION OF THE INVENTION

The soft tip torsion control catheter constructed in accordance with the present invention employs a copolymer composition that has heretofore not been employed in a soft tip torsion control catheter. The physical properties of the present soft tip copolymer composition can be easily modified by altering the relative amounts of the various monomers in the copolymer, making it easily adaptable to the requirements of different catheters. In particular, the composition is advantageously easily modified to exhibit desirable stiffness and memory, and it bonds well to a wide range of preferred body materials. For example, due to its relatively low and sharp melting point, it is more easily bonded to stiffer materials, such as nylon 11 and nylon 12, than commonly used polyamide block copolymers. It also bonds well to maleic anhydride modified polyethylene, unlike polyamide block copolymers, yielding advantages in design choice and ease of manufacture. Moreover, various grades of the soft tip copolymer can be blended with each other, or with various grades of a nylon (e.g., nylon 11 or nylon 12) to provide a wide range of stiffnesses. Polyamide block copolymer compositions do not blend well with each other. As a result, soft tip catheters employing the present copolymer composition exhibit advantages as compared to the prior art.

In one embodiment of the present invention, the present soft tip copolymer composition is used in a torsion control soft tip catheter comprising a tubular body, and a soft, flexible tip member connected to the tubular body. The soft tip member is formed from a material comprising a copolymer of polyamide monomers with monomers of polyamide having lower alkyl side chain groups attached to a polyamide backbone.

More specifically, the copolymer used in the distal catheter soft tip of the invention comprises a first monomer that is a polyamide monomer of the formula:

and a second monomer that is a polyamide side chain monomer of the formula:

where x is from 0 to 11, y is equal to or greater than 1 and z is from 0 to 11, with the proviso that the sum of x, y and z is an integer from 9 to 11. The polyamide monomer is present in an amount of from about 50 to about 90% by weight based on the weight of the first and second monomers, and the side chain monomer is present in an amount of from about 10 to about 50% by weight based on the weight of the monomers. The subscript m is an integer from 9 to 11. The number of side chains in the second monomer is random, but is at least one. Preferably, y is equal to 1. The value of n may be an integer from 2 to 9, and is preferably 6.

In addition to the copolymer, the distal soft tip member may also include radiopaque material, colorants, and other additives known in the art. Suitable colorants, such as titanium oxides, and suitable radiopaque materials, such as bismuth subcarbonate, bismuth oxychloride, bismuth trioxide, tungsten metal and barium sulfate, are commercially available and would be known to those of ordinary skill in the art in view of the instant disclosure.

The catherer body may be formed from a polyamide or other material having suitable properties. Suitable body materials include polyurethane, polyethylene, nylon 11 or nylon 12, or blends of these as is known in the art. In the case of guiding catherers, an innermost tube may be used for improved lubricity. One composition of this lubricious innermost tube is TEFLON® brand polytetrafluoroethylene. Another composition is this lubricious innermost tube is comprised of a vinylic polymer and one of an unsaturated carboxylic acid and an anhydride of the carboxylic acid, in particular, a copolymer of polyethylene and maleic anahydride. The body may include radiopaque material, colorant, and other commonly used additives. Although the bodies of torsion control catherers typically include inner and outer tubes separated by a reinforcing braid to impart good torqueability while retaining adequate flexibility, the present invention contemplates torsion control catherers that may be braided or unbraided.

In a preferred form the present torsion control soft tip catheter comprises a tubular body having two end portions, the body being formed from a nylon having desired stiffness for torqueability, burst strength and longitudinal rigidity. A soft, flexible tip portion is connected to one of the body end portions and is formed of a material that is preferably more flexible than material of the body. The tip portion is formed from a copolymer including a first monomer of polyamide and a second monomer having a polyamide backbone with a seven carbon (heptyl) side chain group as described above.

The present catheter soft tip composition overcomes the problems of the prior art compositions. It has suitably low memory as to enhance guidability while avoiding the danger of puncturing or traumatizing surrounding tissues during use. The physical properties of the present catheter soft tip copolymer can be easily modified to accommodate various needs based on the effect of the side chain groups on the crystallinity of the copolymer. The side chains hinder the crystallinity of the copolymer. By increasing or decreasing the frequency of the side chains, such as by changing the relative percentage of the side chain monomer in the copolymer, the crystallinity and hence, flexibility or softness of the tip can advantageously be modified.

Moreover, by blending the noted copolymer with like copolymers having different percentages of the polyamide side chain monomer, and/or by blending it with various polyamides, one can obtain a material with a wide range of flexibility from that approximating pure nylon 11 or 12, to that of a 50:50 copolymer of polyamide and side chain monomer. Accordingly, the copolymer of the invention may be modified for use in the catheter body when the percentage of polyamide in the copolymer approaches 80% or greater, or when the copolymer is blended with a nylon.

Accordingly, in one embodiment there is provided a torsion control catheter including a tubular body and a soft tip member connected to the tubular body, the tip member material preferably being more flexible than material of the body. The soft tip is formed from a composition comprising a copolymer including a first monomer of polyamide and a second monomer of polyamide having a lower alkyl side chain group attached to a polyamide backbone. Preferably, the first monomer is present in an amount of from about 50% to about 90% by weight, and the second monomer is present in an amount of from about 10% to about 50% by weight, based on the combined weight of the first and second monomers.

Still more preferably, the tip member is formed from a composition comprising a copolymer comprising a first monomer of polyamide of the formula:

and a second monomer that is a polyamide side chain monomer of the formula:

where x is from 0 to 11, y is equal to or greater than 1 and z is from 0 to 11, with the proviso that the sum of x, y and z is an integer from 9 to 11; m is an integer from 9 to 11; n is an integer from 2 to 9, and the polyamide monomer is present in an amount of from about 50 to about 90% by weight based on the weight of the first and second monomers, and the side chain monomer is present in an amount of from about 10 to about 50% by weight based on the weight of the monomers.

In the preferred embodiment, m is 10 or 11 and n is equal to 6, Still more preferably, the sum of x, y and z is equal to 10, m is equal to 10, and n is equal to 6, In one embodiment, the soft tip further includes nylon 11 or nylon 12 blended with the copolymer. In one preferred embodiment, an 80.20 copolymer comprises about 80% by weight of the first monomer and about 20% by weight of the second monomer, based on the combined weight of the first and second monomers. In another preferred embodiment, a 67.33 copolymer comprises about 67% by weight of the first monomer and about 33% by weight of the second monomer, based on the combined weight of the first and second monomers.

In one embodiment, the catheter body is formed from a composition comprising a polyamide such as the nylons described. In another embodiment, the catheter body is formed from a composition comprising a blend of a polyamide and the copolymer. In still another aspect of the invention the catheter body comprises inner and outer tubes having a reinforcing braid disposed therebetween. In all embodiments of the present invention none, one or more tip members may be disposed between the body and the soft tip member comprising the inventive copolymer. Moreover, a tip member may be connected to the soft tip member comprising the inventive copolymer and located more distally with respect to the body than the soft tip member.

In yet another embodiment of the invention a torsion control catheter is characterized by at least one intermediate tip member formed from a composition comprising the copolymer of the present invention with a distal tip member that need not be formed of the copolymer. At least one tubular intermediate tip member is located between the distal tip member and the body. The distal tip member may be formed of the copolymer of the present invention or of any material that is different than the copolymer and has flexibility and other properties suitable for use as a catheter distal tip. The distal tip member is preferably comprised of the 67.33 copolymer or polyurethane.

More specifically, at least the intermediate tip of such a catheter may employ the first monomer in an amount of from about 50% to about 90% by weight, and the second monomer in an amount of from about 10% to about 50% by weight, based on the combined weight of the first and second monomers. In particular, the copolymer may be formed of the 67.33 copolymer or the 80.20 copolymer, blends of these copolymers or blends of these copolymers with a nylon. The catheter body is preferably formed from any suitable material as described above and preferably has a composition comprising a polyamide alone or a polyamide blended with the copolymer. The catheter body may comprise inner and outer tubes having a reinforcing braid disposed therebetween.

In one aspect of this embodiment, the catheter is characterized by an intermediate tip member that is contiguous with the body comprising one of the 80.20 copolymer and a blend of the 80.20 copolymer and a polyamide. At least one of the intermediate tip members containing the copolymer may be disposed such that it is not contiguous with any catheter portion containing nylon 11 or nylon 12. In addition, at least one of the intermediate tip members may be free of nylon 11 and nylon 12. This allows flexibility of design compared to compositions wherein each tip member contains nylon 11 or nylon 12 or is contiguous with a member that contains nylon 11 or nylon 12.

In this embodiment various numbers of intermediate tip members may be disposed between the body and the distal tip member, preferably ranging from one to three. In the case of a catheter comprising two intermediate tip members a first intermediate tip member is contiguous with the body and a second intermediate tip member is disposed between the distal tip member and the first intermediate tip member. In a preferred form of this catheter, the distal tip member is formed of a composition comprising one of a polyurethane and the 67.33 copolymer. The second intermediate tip member is formed of a composition comprising one of the 67.33 copolymer and a blend of the 67.33 copolymer and the 80.20 copolymer. The second intermediate tip member may be free from nylon 11 and nylon 12. The first intermediate tip member is formed of a composition comprising one of the 80.20 copolymer and a blend of the 80.20 copolymer and a polyamide.

In the case of a catheter comprising three intermediate tip members, a first intermediate tip member is contiguous with the body, a second intermediate tip member is connected to the first intermediate tip member, and a third intermediate tip member is disposed between the distal tip member and the second intermediate tip member. In a preferred form of this catheter the distal tip member is formed of a composition comprising one of a polyurethane and the 67.33 copolymer composition. The third intermediate tip member is formed of a composition comprising one of the 67.33 copolymer and a blend of the 67.33 and 80.20 copolymers. The second intermediate tip member is formed of a composition comprising a blend of the 67.33 copolymer and the 80.20 copolymer. The first intermediate tip member is formed of a composition comprising one of the 80.20 copolymer and a blend of the 80.20 copolymer and a polyamide.

The catheter of the present invention preferably includes segments formed of different flexibilities. For example, material of the soft or distal tip member is at least as flexible as material of the body. When an intermediate tip member is used, material of the soft or distal tip member is at least as flexible as material of the intermediate tip member which is at least as flexible as material of the body. Of course, relative flexibilities of various catheter portions are affected by the presence of a braid as well as the presence of inner tubular members.

Another embodiment of the present invention relates to the ability of the copolymer to be blended with itself. A torsion control catheter comprises a tubular body and at least one tip member connected to the body. The at least one tip member is formed from a composition comprising a blend of first and second copolymers each including a first monomer of polyamide and a second monomer of polyamide having a lower alkyl side chain group attached to a polyamide backbone. The first copolymer may have different relative amounts of the first and second monomers than the second copolymer.

Finally, another aspect of the present invention relates to the specific application of a catheter designed for performing angiography. For example, the catheter has a length, size and tip shape (e.g., right or left coronary tip) suitable for performing angiography. The angiographic catheter comprises a tubular body and at least one tip member connected to the body. The at least one tip member is formed from a composition consisting essentially of the copolymer of the present invention. In preferred form the composition further comprises radiopaque material in an amount not greater than about 60% by weight based upon the total weight of the composition, and in particular, the composition excludes nylon 11 and nylon 12. The tip member may be a distal tip member and/or an intermediate tip member.

Other objects, advantages and features of the invention will be apparent from the following description of the preferred embodiments taken in conjunction with the accompanying drawings.

DETAILED DESCRIPTION OF PREFERRED EMBODIMENTS

Figure 1:
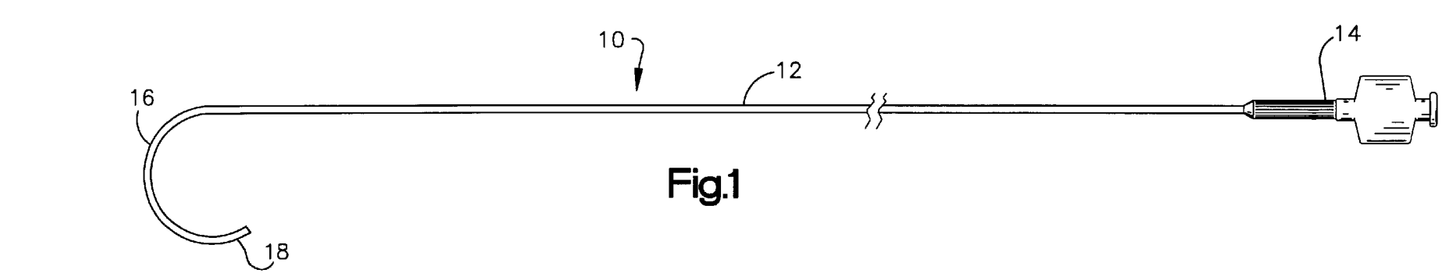
FIG. 1 is a plan view of-a catheter constructed in accordance with the present invention.

Turning now to the drawings and to FIG. 1 in particular, the torsion control soft tip catheter of the present invention is shown generally at 10. The catheter includes a tubular body 12 having a proximal end portion 14 and a distal end portion 16. A soft tip shown generally at 18 is attached to the body 12 at the distal end portion 16 and comprises tip members at least one of which is formed of a copolymer of the present invention or blends thereof. Those skilled in the art will appreciate that the distal end portion 16 of the catheter 10, may be configured in any manner suitable for torsion control catheters. For example, the soft tip 18 may be a pigtail tip, a right coronary tip, a left coronary tip or other suitable tip as is known in the art. Likewise, it would be apparent to those of ordinary skill in the art in view of this disclosure that the nature of the catheter hub at the proximal end portion 14, and the catheter dimensions may vary depending upon the specific use to which the catheter will be put.

Figure 2:
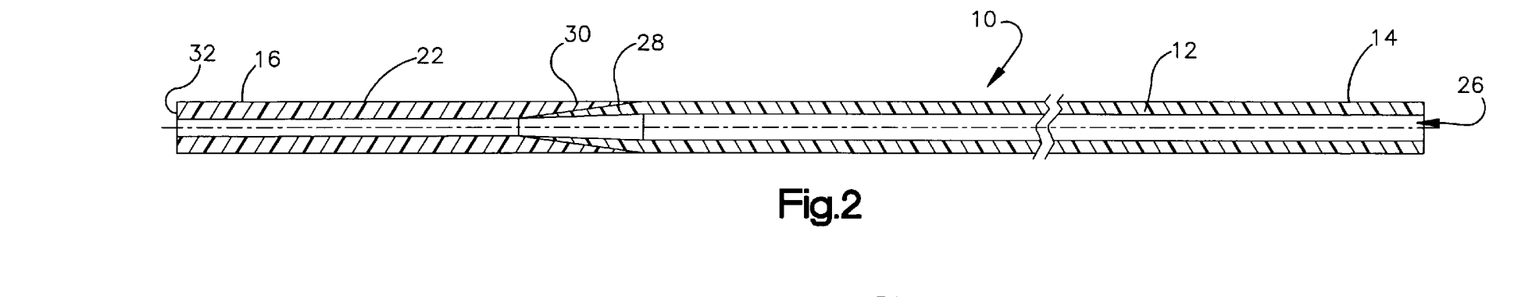
FIG. 2 is a cross-sectional view of a body and a soft tip member connected to the body in a catheter constructed in accordance with the invention.

A preferred embodiment of the present soft tip catheter construction is shown in FIG. 2. The body 12 is a single tubular member and is connected to a soft tip member 22. A lumen 26 is formed along the length of the catheter body 10. The body 12 includes an inwardly tapered end portion 28. The soft tip member 22 has a first outwardly tapered end portion 30 and a second end portion 32. The taper of the first end portion 30 corresponds to and mates with the taper of the end portion 28 of the body 12.

Figure 3:
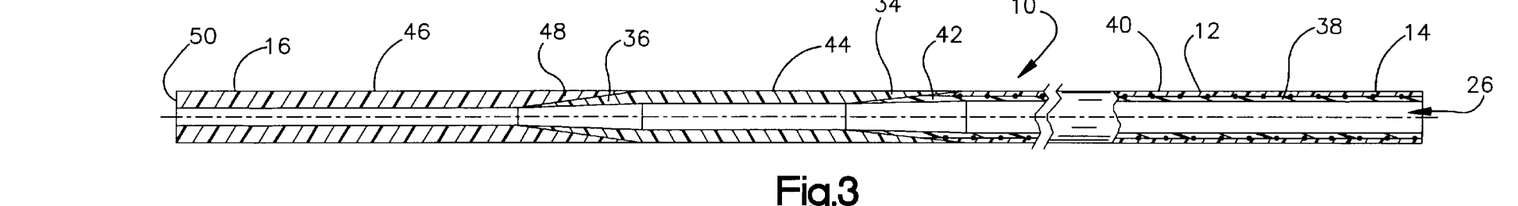
FIG. 3 is a cross-sectional view of a catheter having a body, intermediate and distal soft tip members connected to the body in a catheter constructed in accordance with the invention.

In another embodiment shown in FIG. 3, the catheter 10 includes an intermediate soft tip member 44 connected between a distal tip member 46 and the body 12. As shown, the catheter includes a single intermediate tip 44. However, in all embodiments of the invention described herein there may be numerous intermediate tips of varying stiffness and composition depending upon the particular application to which the catheter is to be put. Thus, while the intermediate tip member 44 is shown directly connected to the distal tip member 46 and the body 12, there may be none, one or more intermediate tip members located between the intermediate tip member 44 and the distal tip member 46 and between the intermediate tip member 44 and the body 12. Moreover, in all embodiments of the present invention regardless of reference to an inventive copolymer-containing tip member as a "distal" tip member or as an "intermediate" tip member, another more distal tip member may be connected to it, i.e., at a more distal location with respect to the body than such inventive tip member, the more distal tip member having a composition that is different than the copolymer or includes the copolymer.

As shown in FIG. 3, the body 12 has an inwardly tapered end portion 42. The intermediate tip member 44 has a first outwardly tapered end portion 34 and a second inwardly tapered end portion 36. The taper of the first end portion 34 corresponds to and mates with the taper of the end portion 42 of the body 12. The distal tip member 46 has a first outwardly tapered end portion 48 and a second end portion 50. The taper of the first end portion 48 of the distal tip member 46 corresponds to and mates with the taper of the second portion 36 of the intermediate tip member 44.

The body 12 may be reinforced by braids or inner reinforcing tube such as TEFLON® brand polytetrafkuorethylene as is sometimes desirable. In this instance, the body 12 includes two concentric tubular members, an inner member 38 and an outer member 40. The inner member 38 is formed from a material that is typically more rigid than the outer member 40. A stainless steel or a nylon fiber braid may be interposed between the inner tubular member 38 and the outer tubular member 40 in the conventional manner to give it sufficient torqueability without detrimentally hindering flexibility. The body may be formed from a known material such as a polyamide. The body may be formed from a known material such as a polyamide. Suitable body materials include nylon 11 or nylon 12, polyurethane and high density polyethylene. When a nylon is used in the body, higher molecular weight nylons are preferable. When an inner tube is used, it may be formed from the same materials or different materials as the outer tube. For example, a nylon outer body tube may employ a nylon inner body tube, or a different material such as TEFLON® depending on the intended use. Alternatively, the body components, whether monotubular or multitubular, braided or unbraided, may be formed from blends of such materials.

The preferred composition of the body is a polyamide. For example, the polyamide is nylon 11 or nylon 12, and still more preferably a high molecular weight nylon 12 such as is commercially available from Huls under the designation L2101F or EMS under the designation L25. Various colorants, radiopaque material, and other additives may be added to the body as is known in the art. In a preferred embodiment the body includes about 10% to about 40%, more preferably about 20% to about 40%, and still more preferably about 33% by weight of a bismuth salt radiopaque material. Similarly, the body may contain from about 10% to about 40%, and still more preferably about 20% by weight of a barium sulfate radiopaque material.

In one embodiment, a distal soft tip member 46 or 22 is connected to the intermediate tip member 44, or body 12. The body 12, intermediate tip member 44 and the distal tip member 22, 46 are all tubular and define a lumen 26 along their length. The various joints and interfaces between inner and outer tubes, and body and tip portions, may be secured to one another as is known in the art, for example by heat welding, heat shrinking and the like.

Regarding fabrication of a catherer using a TEFLON® brand polyetrafluoroethylene lubricious inner tube, the tip members and body are extruded individually in a conventional manner. An innermost TEFLON® tube with a metallic mandrel insert in its lumen is treated with a chemical etching solution or active gas plasma. The body and tip members are mounted over this innermost TEFLON® tube as discussed in U.S. Pat. No. 5,658,262, which is incorporated herein by reference. This is inserted into a TEFLON® sleeve. This assembly is the pulled through a heated die having a diameter of approximately 0.002 inches larger than the desired product diameter. The temperature of the die is 5° to 100° higher than the melt temperature of the highest melting thermoplastic of the assembly. TEFLON® is not such a thermoplastic. The assembly is then cooled and the mandrel and the TEFLON® sleeve are removed.

The copolymer composition of the present invention may be used in one or more of the tip members, i.e., in the soft or distal tip members, intermediate tip members and body, and will now be described. The copolymer of the present invention may be formed from a composition comprising a copolymer of polyamide with side chain polyamide monomers having a lower alkyl, preferably heptyl, side chain group attached to a polyamide backbone of the monomer. More specifically, the copolymer comprises a first monomer of polyamide and a second monomer of polyamide with a side chain group attached to the carbon backbone of the polyamide. The copolymer is a random copolymer, with the side chain monomers or monomer blocks occurring randomly in the polyamide macrostructure. When the soft tip copolymer is to be used in the intermediate tip, the copolymer will include a smaller percentage of the polyamide side chain monomer to provide intermediate stiffness, or the copolymer may be blended with a nylon, or other like copolymers having a higher percentage of polyamide co-monomers to increase stiffness.

The preferred copolymer used in the catheter soft tip of the invention comprises a first monomer that is a polyamide monomer of the formula:

and a second monomer that is a polyamide side chain monomer of the formula:

where x is from 0 to 11, y is equal to or greater than 1 and z is from 0 to 11, with the proviso that the sum of x, y and z is an integer from 9 to 11. The polyamide monomer is present in an amount of from about 50 to about 90% by weight based on the weight of the first and second monomers, and the side chain monomer is present in an amount of from about 10 to about 50% by weight based on the weight of the monomers. The subscript m is an integer from 9 to 11. The subscript n is an integer from 2 to 9, and preferably 6. Preferably, the polyamide monomer is polyamide 11, wherein m is equal to 10. Likewise, the polyamide backbone of the side chain monomer is also preferably polyamide 11, wherein the sum of x, y and z is equal to 10. One or more of the side chain groups are attached randomly to the carbon chain of the polyamide backbone, although y is preferably 1.

Of course, the weight ratios of the monomers in the copolymer may vary depending upon the desired purpose for which the catherer will be used. For example, if one desires to increase the stiffness, the amount of polyamide monomer in the copolymer may be increased. Likewise the copolymer may be blended with, for example, nylon 11 or 12 to increase stiffness. One preferred copolymer comprises about 80% by weight of the first monomer and about 20% by weight of the second monomer having a heptyl side chain, based on the combined weight of the two monomers ("the 80.20 copolymer"), and is commercially available from Atochem under the tradename RILSAN™ brand 80.20 copolymer. This copolymer has an elastic moduls of approximately 350 MPa and a Shore hardness of 62D. All physical properties described herein are at room temperature unless otherwise specified. Another preferred copolymer comprises about 67% by weight of the first monomer and about 33% by weight of the second monomer having a heptyl side chain, based on the combined weight of the two monomers ("the 67.33 copolymer"), and is also commercially available from Atochem under the tradename RISLAN™ brand 67.33 copolymer. This copolymer has an elastic moduls of approximately 180 MPa and a Shore hardness of 53D. The copolymer is prepared by randomly copolymerizing the two monomers in appropriate ratios by a condensation reaction typical of polyamide manufacture as would be apparent to the skilled chemist.

As noted, the soft tip copolymer can be readily blended with other copolymer grades, e.g., a blend of the 80.20 and 67.33 copolymers, or with a nylon, or both, to obtain wide ranges in stiffness. For example, a copolymer that is 80% polyamide and 20% side chain monomer has an elastic modulus on the order of approximately 350 MPa when tested according to ASTM D638. When this copolymer is blended with 50% nylon 12, commercially available from Huls under the designation L2101F, the elastic modulus of the blend becomes approximately 550 MPa (ASTM D638), significantly stiffer than the pure copolymer. Such blends are readily prepared in accordance with known techniques by blending the raw copolymer and the nylon and then extruding the blend into the desired catheter component. For example, the raw copolymer or copolymers, any grade of a nylon that may be blended, and any radiopaque additives, colorant and the like are preferably combined in the desired amounts in a twin screw extruder to form the catheter tubes of the desired blends as would be apparent to those of ordinary skill in the art in view of the instant disclosure.

The following Table sets forth room temperature flexibility (i.e., apparent flex modulus $E_b$) and body temperature flexibility for the 80.20 copolymer and the 67.33 copolymer of the invention compared to a polyamide block copolymer sold under the trademark Pebax® 5533 SA01. The flexibilities were obtained according to the ASTM D747 procedure using a Tinius Olsen Stiffness Tester.

TABLE

| Material | Testing Temperature | $E_b$ (psi) |
|---|---|---|
| 80.20 copolymer | Room | 41620 (4157)[1] |
| 80.20 copolymer | Body (37° C.) | 27441 (2548) |
| 80.20 copolymer annealed[2] | Room | 41031 (5196) |
| 80.20 copolymer annealed[2] | Body | 29966 (3603) |
| 67.33 copolymer | Room | 26267 (1465) |
| 67.33 copolymer | Body | 22084 (2112) |
| 67.33 copolymer annealed[2] | Room | 23007 (1721) |
| 67.33 copolymer annealed[2] | Body | 20256 (1497) |
| Pebax 5533 SA01 | Room | 24160 (1448) |
| Pebax 5533 SA01 | Body | 21583 (1854) |

[1]The values in parentheses are the standard deviations for each value listed.
[2]Annealed at 90° C. for 1 hour.

In determining whether materials will bond to one another so as to be suitable for use in a catheter tip, in addition to knowing the chemical structure of each of the materials, their body temperature flexibilities should also be determined. Without knowing both chemical structure and body temperature flexibility, one cannot accurately determine whether materials will bond to one another for use in a catheter tip.

As illustrated by the above table, the 80.20 material has a substantially higher flex modulus than the polyamide block copolymer. The melting points of the 67.33 and 80.20 copolymers are 153° C and 172° C, respectively. The melting points of high density polyethylene sold under the trademark PLEXAR™, is 134° C. Nylon 12 has a melting point of 178° C. The high density polyethylene used as the lubricious innermost tube may be bonded to the 67.33 and 80.20 copolymers, but will not bond effectively to the PEBAX 5533 SA01 polyamide block copolymer even though the latter has a melting point of 168° C, for example. Polyamide block copolymer also cannot be blended well with itself. Therefore, the polyamide block copolymer is not as commercially useful as the copolymer of the present invention. Especially in the case of the 80.20 copolymer there is a substantial increase in flexibility from room temperature to body temperature compared to the polyamide block copolymer. This shows how difficult it is to predict with accuracy whether materials will bond to one another using only room temperature flexibility data.

Preferred blends of the copolymer and a nylon according to the invention will include nylon 11 or nylon 12 in an amount of from about 10% to about 90% by weight based on the combined weight of the nylon and copolymer. Preferably, the copolymer is blended with from about 10% to about 50% nylon 11 or nylon 12.

Preferred blends of varying copolymer grades according to the invention will include the 80.20 copolymer and the 67.33 copolymer. The blend ratio of the two copolymers may range from about 90% of the 80.20 copolymer to about 90% of the 67.33 copolymer depending upon the desired stiffness.

In modifying the catheter material to a desired stiffness in accordance with the preferred practice, one can start with a composition that is purely formed from the 67.33 copolymer composition. As greater stiffness is desired, one can blend the 67.33 copolymer with increasing amounts of 80.20 copolymer until the composition essentially reaches the maximum stiffness for the blend as the amount of the 80.20 component approaches from about 90% to 100%. It will typically not be advantageous to blend soft copolymers, such as a 50/50 or the 67.33 copolymer, with a nylon due to the difference in melting points. Accordingly, if stiffness greater than that exhibited by, for example, the 80.20 copolymer is desired, one can blend it with increasing amounts of nylon 11 or nylon 12 until the desired stiffness is reached. Blends of the 80.20 copolymer with a nylon are more desirable than blends of, for example, the 67.33 copolymer, because the melting points of the components are closer. As a result of the ability of the soft tip copolymer to be blended with a nylon and other copolymer grades, suitable formulations can be prepared for use in the catheter body as well.

In addition to the copolymer the intermediate and distal tip members may also include radiopaque additives, colorants and the like as would be known to those of ordinary skill in the art. Suitable radiopaque additives include, for example, bismuth subcarbonate, bismuth oxychloride, bismuth trioxide, tungsten metal and barium sulfate to name a few. The distal tip member includes radiopaque material in an amount of from about 10% to about 60% by weight, based on the total weight of the composition. Preferably, the distal tip member will include radiopaque material in an amount of from about 50% to about 60% by weight based upon the total weight of the composition. For example, the radiopaque material may be bismuth subcarbonate present in an amount of about 43% by weight. Preferably, the tip also contains from about 0.02 to about 2% by weight colorant. The intermediate tip members each have radiopaque material in an amount of from about 20% to about 40%. The amount of radiopaque material in all tip members and body may be adjusted to obtain suitable contrast. The foregoing amounts of radiopaque materials are used for the copolymers of the invention, blends thereof, and for polyurethane or other materials suitable for use in a catheter tip.

The intermediate tip members, if any, the body 12, and the distal or soft tip members are extruded into respective tubes in the conventional manner. The end portions of these tubes are preferably cut and formed to include inward or outward tapers. Alternatively, the tubes may have end portions perpendicular to their side walls to form a butt joint. These tubes are then fused together upon application of heat and pressure as is known in the art.

Figure 4:
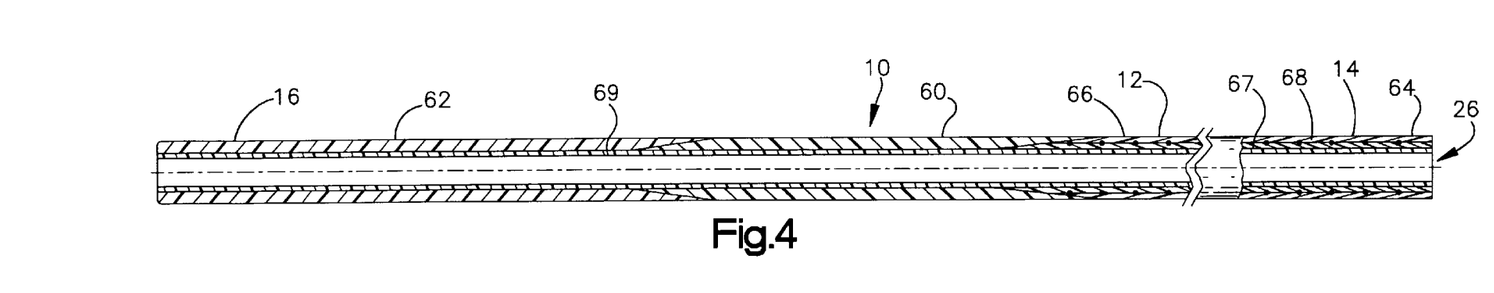
FIG. 4 is a cross-sectional view of another catheter having a body, intermediate and distal tip members connected to the body in a catheter constructed in accordance with the invention.

Referring to FIG. 4, another embodiment of a torsion control soft tip catheter of the present invention has at least one intermediate tip member 60 comprised of the copolymer of the present invention or blends thereof. The intermediate tip member is disposed between a distal tip member 62 and the body 12. Although the distal tip member 62 may be comprised of the copolymer (e.g., the 67.33 copolymer), it is preferably comprised of a material that is different than the copolymer. Suitable materials for the distal tip member would be apparent to those skilled in the art.

The catheter includes the tubular body having a proximal end portion 64 and a distal end portion 66. The distal tip member is attached to the body at the distal end portion. The distal and intermediate tip members are made of materials having suitable flexibility and radiopacity. The material of the distal tip member is preferably more flexible than material of the intermediate tip member to which it is connected and the material of the intermediate tip member is preferably more flexible than material of the body.

The distal tip member is preferably formed of a composition comprising polyurethane. For example, the distal tip member may comprise polyether-polyurethane or polyester-polyurethane composition. One example of a specific formulation of the soft distal tip member may contain 39.7 weight percent of a commercially available polyurethane such as PELLETHANE® 80AE, sold by the Dow Chemical Company; 60 weight percent of bismuth trioxide and 0.3 weight percent of oxidized polyethylene, which is a commercially available and known dispersing agent, release agent and lubricant for the system.

Another example of a specific formulation of the distal tip member comprises 49.83 weight percent of a commercially available polyurethane formulation such as ESTANE® 58271-021 of B.F. Goodrich Corporation, 49.83 weight percent of powdered bismuth subcarbonate and .33 weight percent of the oxidized polyethylene.

Yet another example of a specific formulation of the distal tip member comprises 49.83 weight percent of a commercially available polyurethane formulation such as ESTANE ®58271-021 B.F. Goodrich Corporation, 49.83 weight percent of bismuth trioxide and 0.033 weight percent of the oxidized polyethylene.

It may be desirable to use a finely powdered grade of the radiopaque agent, such as bismuth trioxide, bismuth subcarbonate, barium sulfate, or other material, in the distal tip formulations to provide homogeneity to the polymer formulations to which they are added.

The catheter shown in FIG. 4 is constructed in the manner described herein with respect to the catheter of FIG. 3. The body may be reinforced by braids or an inner reinforcing tube. In this instance, the body includes concentric tubular members, an optional inner member 67 and an outer member 68. The inner member is formed from a material that may be more rigid than the outer member. A stainless steel or a nylon fiber braid may be interposed between the inner tubular member and the outer tubular member in the conventional manner to give it sufficient torqueability without detrimentally hindering flexibility. Alternatively, in the catheters shown in FIGS. 4–6, the inner tubular member may be omitted and the braid may be disposed directly between the outer tubular member and the lubricious innermost tube.

An optional radially innermost tube 69 may also be used. This inner tube is formed of a suitable material effective to decrease the frictional resistance for facilitating advancement of a guidewire, a separate, smaller catheter or other instrument through the catheter. The catheter also has the benefit of the physical properties provided by the inner and/or outer members. Accordingly, the overall catheter may exhibit a desired level of stiffness while still remaining flexible, due to the combined properties of the inner and/or outer members of the catheter tube. At the same time, the frictional characteristics of the walls of the lumen may remain low irrespective of the frictional characteristics of the inner or outer members. This may be accomplished without the use of a coating in the lumen. Coatings are disadvantageous in that they are formed by a complex manufacturing process. The inner member and/or outer member of the catheter and the innermost tube may be coextruded.

Diagnostic catheters, through which fluid is injected, would not ordinarily employ an innermost lubricious tube. However, even diagnostic catheters may benefit from a lubricious inner tube in some applications. For example, in neurological procedures, the guidewire is so small that a TEFLON® brand polytetrafluroethylene coating is not able to be coated onto the guidewire. As a result, diagnostic catheters used in neurogical procedures could benefit from a lubricious innermost tube. Tip members may be used in various numbers and may have various lengths, both long and short, in diagnostic and guiding catheters.

In the case of guiding catheters another catheter, for example, is guided through the guiding catheter. The position of the guiding catheter tip should be maintained at a fixed position relative to the heart, for example. Therefore, care should be taken to gradually vary the flexibility of the catheter tip members, especially in the case of a long tip, to avoid kinking problems that could result in tip movement. Guiding catheters are preferably formed with the lubricious inner tube. One to four tip members are preferably employed for constructing guiding catheters (up to three intermediate tip members) whereas one or two tip members are preferably used for constructing diagnostic catheters (not more than one intermediate tip member). Of course, there may be some applications in which different numbers of catheter tip members other than described, may be used.

On formulation of the lubricious innermost tube is TEFLON®. Another preferred formulation of the lubricious innermost tube comprises a copolymer of a major amount of a vinylic acid or an anhydride thereof. One suitable inner tube composition comprises a polyethylene which contains about 1 to 5 mol% of maleic anhydride units present in the molecule (on a mol percent basis).

More specifically, the lubricious innermost tube material may comprise a high density polyethylene, modified, for example, with the presence of about 1 or 2 mol percent of copolymerized maleic and anhydride units, supplied, for example, by the Quantum Chemical Corporation un the trademark, PLEXAR™. PLEXAR™ brand modified polyethylene resins are conventionally used as tie layer resins for the bonding of dissimilar plastics together in coextruded films. The thickness of the PLEXAR™ innermost lubricious tube ranges from about 0.0005 inches to about 0.006 inches. High density polyethylene is generally understood by those skilled in the art to have a density of at least 0.94 g/cc. A polyethylene containing reactive groups and having at least this density is defined herein as a "high density polyethylene."

The functional groups which are found on the vinylic polymers used in this invention to promote a chemical bond between the innermost lubricious tube and a radially adjacent member may include copolymerized units such as an unsaturated carboxylic acid, or an anhydride thereof, or functional groups which are substituents of vinyl-containing molecules, polymerized or co-polymerized to form the vinylic polymer, for example, hydroxyl in the case of polyvinyl alcohol, or other pendant reactive groups as may be desired to permit the formation of a chemical bond between two plastic materials.

The copolymerized, unsaturated carboxylic acid or anhydride thereof can thus serve as a functional group which bonds a vinylic polymer of the innermost lubricious tube to the material of the radially adjacent member (in the body, intermediate tip, and/or distal tip). This bonding occurs, for example, particularly when the adjacent member is formed of a polyamide or other nitrogen-containing polymer such as the copolymer of the invention. Similarly, such vinylic polymers having acid functional groups may react with hydroxyl-containing polymers of the radially adjacent member, under proper reaction conditions. Such reactions may take place during co-extrusion of the two layers, to form a covalent bond between the innermost lubricious tube and the radially adjacent member.

The innermost lubricious tube and radially adjacent member may be coextruded in a conventional manner. The manufactured tubing may then be assembled in a conventional manner to form the catheter of the invention. To prevent the braid from penetrating through the modified polyethylene material of the innermost lubricious tube and into the lumen as a result of the heat present in the extrusion process, the modified polyethylene material may be cross-linked in a manner that would be apparent to the skilled chemist in view of this disclosure.

The modified polyethylene material of the innermost tube advantageously bonds well with the copolymer of the intermediate or distal tip members and to the material of the body (e.g., a polyamide). This bonding enables the tip of the catheter (including distal and intermediate tip members) to be constructed of various lengths. The combined length of the distal member and any intermediate tip members may range from about 0.6 cm for short tips to a length ranging from about 20 cm to about 40 cm for long tips. The good bonding between the modified polyethylene innermost tube material and the copolymer of the distal tip member enables the tip to be fabricated to a greater length. If the modified polyethylene inner layer material does not bond well with the material of a tip member, the tip member will not be disposed around the innermost lubricious tube. As a result, such a tip member with a modified polyethylene innermost tube would have a short length, since using long tip members without a lubricious inner layer may cause a guidewire or the like guided through the catheter to encounter excessive frictional resistance.

In view of the ability of the modified polyethylene innermost tube material to bond to the copolymer, tips formed of the copolymer may have greater lengths. The modified polyethylene innermost tube may extend across a portion of the distal tip member, but preferably extends along the entire length of the distal tip member. Long tip members possible as a result of the present invention may have utility in specific medical applications such as in neurological procedures.

The modified polyethylene innermost tube material preferably extends up to a polyurethane distal tip member. When the distal tip member is formed of the copolymer of the present invention (e.g., the 67.33 copolymer), the modified polyethylene inner layer material preferably extends the entire length of the distal tip member to the end of the catherer. A TEFLON® brand polytetrafluoroethylene innermost tube may be formed via chemical etching and the like, so as to bond to polyurethane and the copolymer.

Figure 5:
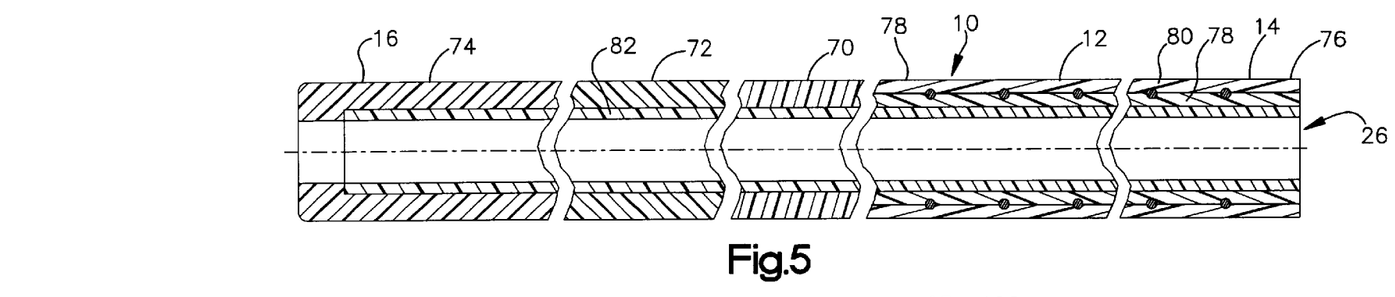
FIG. 5 is a cross-sectional view of a catheter having a body, two intermediate tip members and a distal tip member connected to the body in a catheter constructed in accordance with the invention.

FIG. 5 shows yet another embodiment of the catheter of the present invention having two intermediate tip members 70, 72 at least one of which is comprised of the copolymer of the present invention or blends thereof. Although the distal tip member may be comprised of the copolymer (e.g., the 67.33 copolymer) the distal tip member is preferably comprised of a different material than the copolymer. Suitable compositions for the distal tip member would be apparent to those skilled in the art. For example, the polyurethane composition described in connection with the distal tip member of FIG. 4, may be used. The intermediate tip members are disposed between the body 12 and a distal tip member 74. The tubular body 12 has a proximal end portion 76 and a distal end portion 78. The distal tip member 74 is attached at the distal end portion of the body. In preferred form, the first intermediate tip member 70 is connected to the body, followed by the second intermediate tip member 72 disposed between the distal tip member 74 and the first intermediate tip member 72. The distal and intermediate tip members are made of materials having suitable flexibility and radiopacity. Material of the distal tip member is preferably more flexible than material of the second intermediate tip member which is more flexible than material of the first intermediate tip member, which in turn is more flexible than material of the body.

The tip members of FIG. 5 may be configured and connected in the manner described with respect to FIGS. 3 and 4. The body may include an optional inner tube member 78 and an outer member 80. An optional innermost lubricious tube 82 formed of a suitable material may be used to decrease the frictional resistance. The inner and outer members 78, 80 and the innermost lubricious tube 82 of the catherer may be coextruded. One formulation of the innermost tube material is TEFLON®, fabrication of the catherer formed with TEFLON® innermost tube being described above. A preferred formulation of the innermost tube comprises the modified polyethylene material described in connection with FIG. 4.

Figure 6:
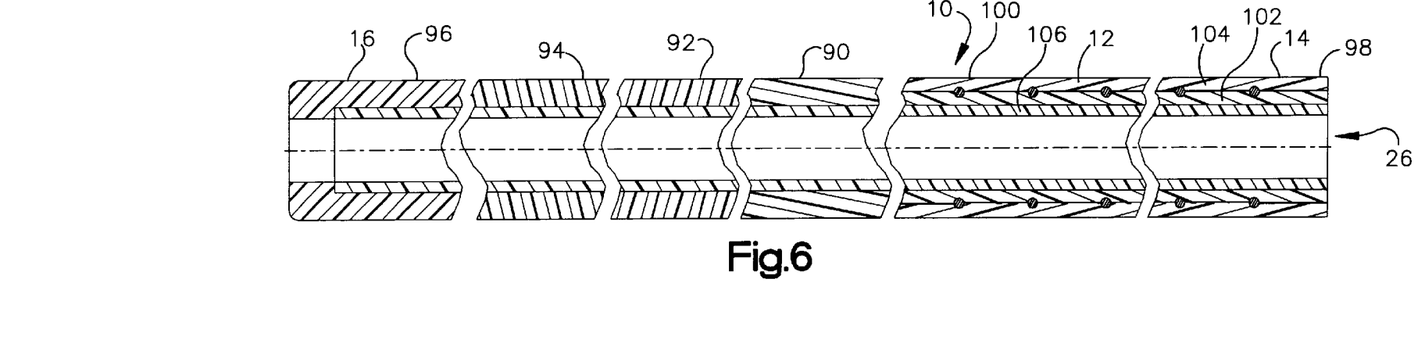
FIG. 6 is a cross-sectional view of a catheter having a body, three intermediate tip members and a distal tip member connected to the body in a catheter constructed in accordance with the invention.

FIG. 6 shows a further embodiment of a catheter constructed in accordance with the present invention. The catheter has three intermediate tip members 90, 92, 94, at least one of which is comprised of the copolymer of the present invention or blends thereof. The intermediate tip members are disposed between the body 12 and a distal tip member 96. Although the distal tip member may be comprised of the copolymer (e.g., the 67.33 copolymer), the distal tip member is preferably comprised of a different material than the copolymer. Suitable compositions for the distal tip member would be apparent to those skilled in the art. For example, the distal tip member may comprise the polyurethane composition described above in connection with the distal tip member of FIG. 4.

The body 12 has a proximal end portion 98 and a distal end portion 100. The distal tip member 96 is attached at the distal end portion of the body. In preferred form, the first intermediate tip member 90 is directly connected to the body 12. The second intermediate tip member 92 has one end connected to the first intermediate tip member. A third intermediate tip member 94 is disposed between the distal tip member and the second intermediate tip member. The distal and intermediate tip members are made of materials having suitable flexibility and radiopacity. Material of the distal tip member is preferably more flexible than material of the third intermediate tip member, which is more flexible than material of the second intermediate tip member. The material of the second intermediate tip member is preferably more flexible than material of the first intermediate tip member, which in turn is more flexible than material of the body.

The tip members of the catherer shown in FIG. 6 are constructed and connected to one another as described in connection with FIGS. 3 and 4. The body may include an optional inner tubular member 102 and an outer tubular member 104. An optional innermost lubricious tube 106 is formed of suitable material effective to decrease the frictional resistance. The inner and outer tubular members and the innermost lubricious tube of the catherer may be coextruded. One formulation of the lubricious innermost tube material is TEFLON®, a catherer with a TEFLON® innermost tube being formed as described above. A preferred formulation of the lubricious innermost tube comprises the modified polyethylene material described in connection with FIG. 4. Although the specific catherers formed in FIGS. 4–6 preferably have an innermost lubricious tube, it will be appreciated that the catherers shown in FIGS. 4–6 may be formed without the lubricious innermost tube.

Referring now to catheters of preferred construction, when intermediate tip members are used, the intermediate tip member that is directly bonded to the body is preferably formed of a composition comprising the 80.20 copolymer alone or a blend of the 80.20 copolymer and a polyamide (e.g., nylon 11 or nylon 12). Any additional intermediate tip members are selected to have compositions which effect a gradual increase in flexibility progressing toward the most flexible distal tip member. It will be apparent that flexibility of parts of the catheter is affected by the presence of the reinforcing braid and any inner tubes. The braid may extend only in the body, as well as in the body and any of the tip members. The gradual change in flexibility is preferably achieved using a blend of the 80.20 and 67.33 copolymers and decreasing the relative amount of the 80.20 copolymer in successive intermediate tip members toward the distal tip member. The number of intermediate tip members, the flexibility, and hence material of each tip member, and the length of each tip member, are dependent upon the shape of the curve in the tip portion of the catheter, which of course is dictated by the requirements of the particular medical procedure.

More specifically, as to the preferable composition of the catheter of FIG. 4, which employs one intermediate tip member, the distal tip member is formed of a composition comprising polyurethane or the 67.33 copolymer, the intermediate tip member is formed of a composition comprising the 80.20 copolymer alone or blended with a polyamide (e.g., nylon 11 or 12), and the body is formed of a composition comprising a polyamide. The catheter of FIG. 4 even more preferably has the intermediate tip member formed of a composition comprising the 67.33 copolymer and the distal tip member formed of a composition comprising polyurethane. The catheter of FIG. 4 may be used as a diagnostic catheter, for example, without the lubricious innermost tube, or as a guiding catheter.

A preferred composition of the catheter of FIG. 5, which employs two intermediate tip members, comprises the distal tip member formed of a composition comprising polyurethane, the second intermediate tip member formed of a composition comprising the 67.33 copolymer, the first intermediate tip member formed of a composition comprising the 80.20 copolymer alone or blended with a polyamide (e.g., nylon 11 or 12), and the body formed of a composition comprising a polyamide. Another preferred composition of the catheter of FIG. 5 comprises the distal tip member formed of a composition comprising the 67.33 copolymer, the second intermediate tip member formed of a composition comprised of a blend of the 67.33 and 80.20 copolymers, the first intermediate tip member formed of a composition comprising the 80.20 copolymer alone or blended with a polyamide and the body formed of a composition comprising a polyamide. This catheter is preferably used as a guiding catheter.

A preferred composition of the catheter of FIG. 6, which includes three intermediate tip members, preferably comprises the distal tip member formed of a composition comprising polyurethane, the third intermediate tip member formed of a composition comprising the 67.33 copolymer, the second intermediate tip member formed of a composition comprising a blend of the 80.20 and 67.33 copolymers, the first intermediate tip member formed of a composition comprising the 80.20 copolymer alone or blended with a polyamide, and the body formed of a composition comprising a polyamide. Another preferred composition of the catheter of FIG. 6 comprises a distal tip member formed of a composition comprising the 67.33 copolymer, the third intermediate tip member formed of a composition comprising a blend of the 67.33 and 80.20 copolymers, the second intermediate tip member formed of a composition comprising a blend of the 67.33 and 80.20copolymers with a greater amount of the 80.20 copolymer than the third intermediate tip member, the first intermediate tip member formed of a composition comprising the 80.20 copolymer alone or blended with a polyamide, and the body formed of a composition comprising a polyamide. This catheter is preferably used as a guiding catheter.

While the invention has been described in its preferred form with some degree of particularity, it will be apparent to those of ordinary skill in-the art that many modifications may be made thereto without departing from the scope of the invention, which scope is to be accorded the broadest interpretation of the appended claims so as to encompass all equivalent structures and compositions.

What is claimed is:

1. A torsion control catheter including a tubular body and a soft tip member connected to the tubular body, said tip member being more flexible than said body, wherein said soft tip is formed from a composition comprising a copolymer including a first monomer of polyamide and a second monomer of polyamide having a lower alkyl side chain group attached to a polyamide backbone, and wherein said tip comprises a blend of a first copolymer comprising about 80% by weight of said first monomer and about 20% by weight of said second monomer, based on the combined weight of said first and second monomers, and a second copolymer comprising about 67% by weight of said first monomer and about 33% by weight of said second monomer, based on the combined weight of said first and second monomers.

2. The catheter according to claim 1 wherein said tip further includes nylon 11 or nylon 12 blended with said first and second copolymers.

3. The catheter according to claim 1 wherein said catheter body comprises inner and outer tubes having a reinforcing braid disposed therebetween.

4. The catheter according to claim 1 comprising a tubular intermediate tip member connected at one end to said soft tip member and at an opposite end to said body, said soft tip member being more flexible than said intermediate tip member and said intermediate tip member being more flexible than said body.

5. A torsion control catheter including a tubular body and a soft tip member connected to the tubular body, said tip member being more flexible than said body, wherein said soft tip is formed from a composition comprising a copolymer including a first monomer of polyamide and a second monomer of polyamide having a lower alkyl side chain group attached to a polyamide backbone, and wherein said catheter body is formed from a composition comprising a blend of a nylon and said copolymer.

6. A torsion control catheter including a tubular body and a soft tip member connected to the tubular body, said tip member being more flexible than said body, wherein said soft tip is formed from a composition comprising a copolymer including a first monomer of polyamide and a second monomer of polyamide having a lower alkyl side chain group attached to a polyamide backbone, wherein the catheter further includes a tubular intermediate tip member connected at one end to said soft tip member and at an opposite end to said body, the body being stiffer than the intermediate tip member and the intermediate tip member being stiffer than the soft tip member, and wherein the intermediate tip member is formed from a material comprising said copolymer.

7. A torsion control catheter including a tubular body and a tubular soft tip member connected at an end to said body, said tip member being more flexible than said body and being formed from a composition comprising a copolymer comprising a first monomer of polyamide of the formula:

and a second monomer that is a polyamide side chain monomer of the formula:

where x is from 0 to 11, y is equal to or greater than 1 and z is from 0 to 11, with the proviso that the sum of x, y and z is an integer from 9 to 11; m is an integer from 9 to 11; and n is an integer from 2 to 9, and wherein said tip comprises a blend of a first copolymer comprising about 80% by weight of said first monomer and about 20% by weight of said second monomer, based on the combined weight of said first and second monomers, and a second copolymer comprising about 67% by weight of said first monomer and about 33% by weight of said second monomer, based on the combined weight of said first and second monomers.

8. The catheter according to claim 7 wherein the sum of x, y and z is equal to 10, m is equal to 10, and n is equal to 6.

9. The catheter according to claim 7 wherein m is 10 or 11.

10. The catheter according to claim 7 wherein n is equal to 6.

11. The catheter according to claim 7 wherein said tip further includes nylon 11 or nylon 12 blended with said first and second copolymers.

12. The catheter according to claim 7 wherein said catheter body is formed from a composition comprising a nylon.

13. The catheter according to claim 7 wherein said catheter body comprises inner and outer tubes having a reinforcing braid disposed therebetween.

14. The catheter according to claim 7 wherein the catheter further includes a tubular intermediate tip member connected at one end to said soft tip member and at an opposite end to said body, said soft tip member being more flexible than said intermediate tip member and said intermediate tip member being more flexible than said body.

15. A torsion control catheter according to claim 14 wherein said intermediate tip member is formed from a material comprising said copolymer.

16. A torsion control catheter including a tubular body and a tubular soft tip member connected at an end to said body, said tip member being more flexible than said body and being formed from a composition comprising a copolymer comprising a first monomer of polyamide of the formula:

and a second monomer that is a polyamide side chain monomer of the formula:

where x is from 0 to 11, y is equal to or greater than 1 and z is from 0 to 11, with the proviso that the sum of x, y and z is an integer from 9 to 11; m is an integer from 9 to 11; n is an integer from 2 to 9, and said first monomer is present in an amount of from about 50 to about 90% by weight based on the weight of said first and second monomers, and said second monomer is present in an amount of from about 10 to about 50% by weight based on the weight of said first and second monomers, and wherein said catheter body is formed from a composition comprising a blend of a nylon and said copolymer.

17. A torsion control catheter including a tubular body and a soft tip member connected to the tubular body, wherein said soft tip member is formed from a composition comprising a copolymer including a first monomer of polyamide and a second monomer of polyamide having a lower alkyl side chain group attached to a polyamide backbone.

18. The catheter according to claim 17 wherein said first monomer is present in an amount of from about 50% to about 90% by weight, and said second monomer is present in an amount of from about 10% to about 50% by weight, based on the combined weight of said first and second monomers.

19. The catheter according to claim 17 wherein said copolymer comprises about 80% by weight of said first monomer and about 20% by weight of said second monomer, based on the combined weight of said first and second monomers.

20. The catheter according to claim 17 wherein said copolymer comprises about 67% by weight of said first monomer and about 33% by weight of said second monomer, based on the combined weight of said first and second monomers.

21. The catheter according to claim 17 wherein said soft tip further includes nylon 11 or nylon 12 blended with said copolymer.

22. The catheter according to claim 11 wherein said catheter body is formed from a composition comprising a polyamide.

23. The catheter according to claim 17 wherein said catheter body comprises inner and outer tubes having a reinforcing braid disposed therebetween.

24. The catheter according to claim 17 further comprising at least one tubular intermediate tip member located between said soft tip member and said body.

25. The catheter according to claim 24 wherein the at least one said intermediate tip member is formed from a material comprising said copolymer.

26. The catheter according to claim 25 wherein said copolymer in said soft tip is at least as flexible as said copolymer in said intermediate tip which is at least as flexible as material of said body.

27. The catheter according to claim 17 further comprising at least one tip member connected to said soft tip member at a more distal location with respect to said body than said soft tip member.

28. The catheter according to claim 17 wherein said soft tip member is tubular, comprising an innermost tube around which said soft tip member is disposed, said innermost tube being formed of a composition comprising a vinylic polymer and one of an unsaturated carboxylic acid and an anhydride of said carboxylic acid.

29. The catheter according to claim 28 wherein the composition of said innermost tube comprises a copolymer of polyethylene and maleic anhydride.

30. The catheter according to claim 17 wherein said copolymer of said soft tip is at least as flexible as material of said body.

31. A torsion control catheter including a tubular body and a soft tip member connected at an end to said body, wherein said soft tip member is formed from a composition comprising a copolymer comprising a first monomer of polyamide of the formula:

and a second monomer that is a polyamide side chain monomer of the formula:

where x is from 0 to 11, y is equal to or greater than 1 and z is from 0 to 11, with the proviso that the sum of x, y and z is an integer from 9 to 11; m is an integer from 9 to 11; and n is an integer from 2 to 9, and said first monomer is present in an amount of from about 50 to about 90% by weight based on the weight of said first and second monomers, and said second monomer is present in an amount of from about 10 to about 50% by weight based on the weight of said first and second monomers.

32. The catheter according to claim 31 wherein the sum of x, y and z is equal to 10, m is equal to 10, and n is equal to 6.

33. The catheter according to claim 32 wherein said copolymer comprises about 80% by weight of said first monomer and about 20% by weight of said second monomer, based on the combined weight of said first and second monomers.

34. The catheter according to claim 32 wherein said copolymer comprises about 67% by weight of said first monomer and about 33% by weight of said second monomer, based on the combined weight of said first and second monomers.

35. The catheter according to claim 32 wherein the catheter further includes at least one tubular intermediate tip member located between said soft tip member and said body.

36. The catheter according to claim 35 wherein the at least one said intermediate tip member is formed from a material comprising said copolymer.

37. The catheter according to claim 36 wherein said copolymer in said soft tip is at least as flexible as said copolymer in said intermediate tip which is at least as flexible as material of said body.

38. The catheter according to claim 31 wherein m is 10 or 11.

39. The catheter according to claim 31 wherein n is equal to 6.

40. The catheter according to claim 31 wherein said soft tip further includes nylon 11 or nylon 12 blended with said copolymer.

41. The catheter according to claim 31 wherein said copolymer comprises about 80% by weight of said first monomer and about 20% by weight of said second monomer, based on the combined weight of said first and second monomers.

42. The catheter according to claim 31 wherein said copolymer comprises about 67% by weight of said first monomer and about 33% by weight of said second monomer, based on the combined weight of said first and second monomers.

43. The catheter according to claim 31 wherein said catheter body is formed from a composition comprising a polyamide.

44. The catheter according to claim 31 wherein said catheter body comprises inner and outer tubes having a reinforcing braid disposed therebetween.

45. The catheter according to claim 31 wherein said copolymer of said soft tip is at least as flexible as material of said body.

46. A catheter adapted to perform angiography comprising a tubular body and a soft tip member connected to said body, wherein said soft tip member is formed from a composition consisting essentially of a copolymer including a first monomer of polyamide and a second monomer of polyamide having a lower alkyl side chain group attached to a polyamide backbone.

47. The catheter according to claim 46 wherein the composition further comprises radiopaque material in an amount not greater than about 60% by weight based upon the total weight of the composition.

48. The catheter according to claim 47 with the proviso that the composition excludes nylon 11 and nylon 12.

49. The catheter according to claim 46 wherein said tip member is selected from the group consisting of a distal tip member, at least one intermediate tip member disposed between a distal tip member and said body, and a combination thereof.

50. A torsion control catheter comprising a tubular body, a distal tip member, and at least one tubular intermediate tip member located between said distal tip member and said body, wherein the at least one said intermediate tip member is formed from a composition comprising a copolymer including a first monomer of polyamide and a second monomer of polyamide having a lower alkyl side chain group attached to a polyamide backbone.

51. The catheter according to claim 50 wherein said first monomer is present in an amount of from about 50% to about 90% by weight, and said second monomer is present in an amount of from about 10% to about 50% by weight, based on the combined weight of said first and second monomers.

52. The catheter according to claim 50 wherein said copolymer comprises about 80% by weight of said first monomer and about 20% by weight of said second monomer, based on the combined weight of said first and second monomers.

53. The catheter according to claim 50 wherein said copolymer comprises about 67% by weight of said first monomer and about 33% by weight of said second monomer, based on the combined weight of said first and second monomers.

54. The catheter according to claim 50 wherein the at least one said intermediate tip member further includes nylon 11 or nylon 12 blended with said copolymer.

55. The catheter according to claim 50 wherein the at least one said intermediate tip member comprises a blend of a first copolymer comprising about 80% by weight of said first monomer and about 20% by weight of said second monomer, based on the combined weight of said first and second monomers, and a second copolymer comprising about 67% by weight of said first monomer and about 33% by weight of said second monomer, based on the combined weight of said first and second monomers.

56. The catheter according to claim 50 wherein said catheter body is formed from a composition comprising a polyamide.

57. The catheter according to claim 50 wherein said catheter body is formed from a composition comprising a blend of a nylon and said copolymer.

58. The catheter according to claim 50 wherein said catheter body comprises inner and outer tubes having a reinforcing braid disposed therebetween.

59. The catheter according to claim 50 wherein the at least one said intermediate tip member that contains said copolymer is not contiguous with any catheter portion containing nylon 11 or nylon 12.

60. The catheter according to claim 50 wherein the at least one said intermediate tip member is disposed around an innermost tube formed of a composition comprised of a vinylic polymer and one of an unsaturated carboxylic acid and an anhydride of said carboxylic acid.

61. The catheter according to claim 60 wherein said innermost tube comprises a copolymer of polyethylene and maleic anhydride.

62. The catheter according to claim 50 wherein said distal tip member is tubular and is disposed around an innermost tube formed of a composition comprising a vinylic polymer and one of an unsaturated carboxylic acid and an,anhydride of said carboxylic acid.

63. The catheter according to claim 62 wherein said innermost tube comprises a copolymer of polyethylene and maleic anhydride.

64. The catheter according to claim 50 wherein said distal tip member is formed of a material that is different than said copolymer.

65. The catheter according to claim 50 wherein said distal tip member is formed of a material comprising polyurethane.

66. The catheter according to claim 50 wherein said distal tip member is formed of a composition comprising said copolymer.

67. The catheter according to claim 50 wherein one said intermediate tip member that is contiguous with said body is formed of a composition comprising one of (1) an 80.20 composition of said copolymer comprising about 80% by weight of said first monomer and about 20% by weight of said second monomer, based on the combined weight of said first and second monomers, and (2) a blend of the 80.20 copolymer and a polyamide.

68. The catheter according to claim 50 wherein the at least one said intermediate tip member comprises a first intermediate tip member contiguous with said body and a second intermediate tip member disposed between said distal tip member and said first intermediate tip member.

69. The catheter according to claim 68 wherein said distal tip member is formed of a composition comprising one of a polyurethane and a 67.33 formulation of said copolymer comprising about 67% by weight of said first monomer and about 33% by weight of said second monomer, based on the combined weight of said first and second monomers, said second intermediate tip member is formed of a composition comprising one of the 67.33 copolymer and a blend of the 67.33 copolymer and an 80.20 formulation of said copolymer comprising about 80% by weight of said first monomer and about 20% by weight of said second monomer, based on the combined weight of said first and second monomers, and said first intermediate tip member is formed of a composition comprising one of the 80.20 copolymer and a blend of the 80.20 copolymer and a polyamide.

70. The catheter according to claim 68 with the proviso that the composition of said second intermediate tip member is free of nylon 11 and nylon 12.

71. The catheter according to claim 50 wherein the at least one said intermediate tip member comprises a first intermediate tip member contiguous with said body, a second intermediate tip member connected to said first intermediate tip member, and a third intermediate tip member disposed between said distal tip member and said second intermediate tip member.

72. The catheter according to claim 71 wherein said distal tip member is formed of a composition comprising one of a polyurethane and a 67.33 formulation of said copolymer comprising about 67% by weight of said first monomer and about 33% by weight of said second monomer, based on the combined weight of said first and second monomers, said third intermediate tip member is formed of a composition comprising one of the 67.33 copolymer and a blend of the 67.33 copolymer and an 80.20 formulation of said copolymer comprising about 80% by weight of said first monomer and about 20% by weight of said second monomer, based on the combined weight of said first and second monomers, said second intermediate tip member is formed of a composition comprising a blend of the 67.33 copolymer and the 80.20 copolymer, and said first intermediate tip member is formed of a composition comprising one of the 80.20 copolymer and a blend of the 80.20 copolymer and a polyamide.

73. The character according to claim 71 with the proviso that the composition of said second intermediate tip member is free of nylon 11 and nylon 12.

74. The catheter according to claim 50 wherein material of said soft tip is at least as flexible as said copolymer in said intermediate tip which is at least as flexible as material of said body.

75. The catheter according to claim 50 further comprising at least one tip member connected to said distal tip member at a more distal location with respect to said body than said distal tip member.

76. A torsion control catheter comprising a tubular body and at least one tip member connected to said body, wherein the at least one said tip member is formed of a composition comprising a blend of first and second copolymers each including a first monomer of polyamide and a second monomer of polyamide having a lower alkyl side chain group attached to a polyamide backbone.

77. The catheter according to claim 76 wherein said first copolymer has different relative amounts of said first monomer and said second monomer than said second copolymer.

78. A torsion control catheter comprising a tubular body and at least one tip member connected to the body, wherein the at least one tip member is selected from the group consisting of:
  (i) a tip member formed of a composition comprising a copolymer including a first monomer of polyamide and a second monomer of polyamide having a lower alkyl side chain group attached to a polyamide backbone,
  (ii) at least one intermediate tip member disposed between said body and a distal tip member, the at least one said intermediate tip member being formed of a composition comprising a copolymer including a first monomer of polyamide and a second monomer of polyamide having a lower alkyl side chain group attached to a polyamide backbone, and
  (iii) a tip member comprising a blend of two copolymers each comprising a first monomer of polyamide and a second monomer of polyamide having a lower alkyl side chain group attached to a polyamide backbone, and wherein each said copolymer has a composition selected from the group consisting of:
  (iv) a first composition comprising a first monomer of polyamide and a second monomer of a branched polyamide having a lower alkyl side chain group attached to a polyamide backbone, wherein said copolymer comprises about 80% by weight of said first monomer and about 20% by weight of said second monomer,
  (v) a second composition comprising a copolymer including a first monomer of polyamide and a second monomer of a branched polyamide having a lower alkyl side chain group attached to a polyamide backbone, wherein said copolymer comprises about 67% by weight of said first monomer and about 33% by weight of said second monomer, and
  (vi) a third composition comprising a copolymer including a first monomer of polyamide and a second monomer of a branched polyamide having a lower alkyl side chain group attached to a polyamide backbone further blended with nylon, and wherein the body is selected from the group consisting of:
  (vii) a body comprising polyamide,
  (viii) a body comprising a blend of polyamide and a copolymer including a first monomer of polyamide and a second monomer of a branched polyamide having a lower alkyl side chain group attached to a polyamide backbone, and
  (ix) a body comprising inner and outer tubes having a reinforcing braid disposed therebetween.

79. A torsion control catheter including a tubular body and at least one tip member connected to said body, wherein the at least one said tip member is formed of a composition comprising a copolymer including a first monomer of polyamide and a second monomer of polyamide having a lower alkyl side chain group attached to a polyamide backbone.

80. The catheter according to claim 79 wherein the at least one said tip member is disposed between a distal tip member and said body.

81. The catheter according to claim 79 wherein the at least one said tip member is a distal tip member.

82. A torsion control catheter comprising a tubular body, a distal tip member, and at least one tubular intermediate tip member located between sad distal tip member is formed from a composition comprising a copolymer comprising a first monomer of polyamide of the formula:

$$-[N-(CH_2)_{\overline{m}}-C]-$$
$$\phantom{-[}|\phantom{-(CH_2)_{\overline{m}}-}\|$$
$$\phantom{-[}H\phantom{-(CH_2)_{\overline{m}}-}O$$

and a second monomer that is a polyamide side chain monomer of the formula:

$$-[N-(CH_2)_{\overline{x}}-(CH)_{\overline{y}}-(CH_2)_{\overline{z}}-C]-$$
$$\phantom{-[}|\phantom{-(CH_2)_{\overline{x}}-}|\phantom{(CH)_{\overline{y}}-(CH_2)_{\overline{z}}-}\|$$
$$\phantom{-[}H\phantom{-(CH_2)_{\overline{x}}-}(CH_2)_n\phantom{-(CH_2)_{\overline{z}}-}O$$
$$\phantom{-[-(CH_2)_{\overline{x}}-}|$$
$$\phantom{-[-(CH_2)_{\overline{x}}-}CH_3$$

where x is from 0 to 11, y is equal to or greater than 1 and z is from 0 to 11, with the proviso that the sum of x, y and z is an integer from 9 to 11; m is an integer from 9 to 11; and n is an integer from 2 to 9, and said first monomer is present in an amount of from about 50 to about 90% by weight based on the weight of said first and second monomers, and said second monomer is present in an amount of from about 10 to about 50% by weight based on the weight of said first and second monomers.

* * * * *